United States Patent
Nilsson

[11] Patent Number: 5,707,367
[45] Date of Patent: Jan. 13, 1998

[54] CATHETER COMPRISED OF OR INCLUDING ELECTRICALLY CONDUCTIVE SYNTHETIC MATERIAL

[76] Inventor: Leif Nilsson, Blabarsvagen 1, S-260 40, Viken, Sweden

[21] Appl. No.: 505,346

[22] PCT Filed: Feb. 24, 1994

[86] PCT No.: PCT/SE94/00154

§ 371 Date: Oct. 18, 1995

§ 102(e) Date: Oct. 18, 1995

[87] PCT Pub. No.: WO94/19046

PCT Pub. Date: Sep. 1, 1994

[30] Foreign Application Priority Data

Feb. 26, 1993 [SE] Sweden .................. 9300655

[51] Int. Cl.⁶ ................ A61M 5/32; A61M 1/00
[52] U.S. Cl. .................. 604/265; 604/328; 607/116
[58] Field of Search .................. 607/113, 116, 607/126, 128; 604/265, 328, 329, 330, 21

[56] References Cited

U.S. PATENT DOCUMENTS

| | | | |
|---|---|---|---|
| 5,007,437 | 4/1991 | Sterzer | 128/786 |
| 5,295,979 | 3/1994 | DeLaurentis et al. | 604/328 |
| 5,328,954 | 7/1994 | Sarangapani | 428/423.1 |

FOREIGN PATENT DOCUMENTS

| | | |
|---|---|---|
| WO 86/05103 | 9/1986 | WIPO. |
| WO 91/00074 | 1/1991 | WIPO. |
| WO 91/00118 | 1/1991 | WIPO. |

*Primary Examiner*—Robert A. Clarke
*Attorney, Agent, or Firm*—Cowan, Liebowitz & Latman, P.C.

[57] ABSTRACT

A catheter for insertion into a human urethra comprises an elongated open-ended hollow body of circular cross-section produced from a suitable synthetic material, and the catheter body has provided along its length at least one, preferably two, resilient thickenings or projections (11; 12, 13; 14) which surround the body and project radially outwards therefrom and which are intended to lie against the inner walls of the urethra. Both the catheter body (10) and the thickening or thickenings (11; 12) are comprised of an electrically conductive synthetic material, or include an electrically conductive material.

6 Claims, 1 Drawing Sheet

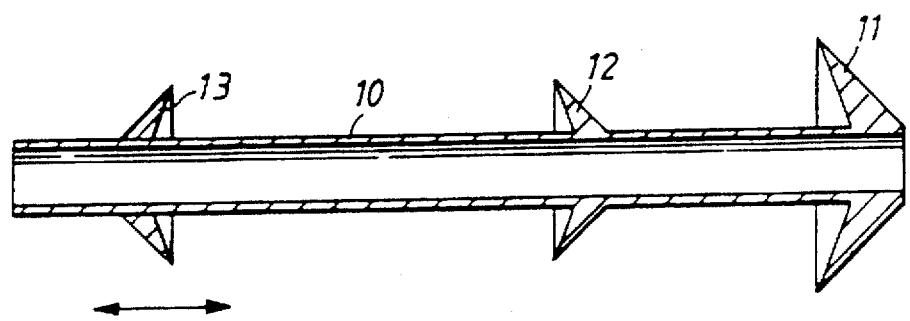
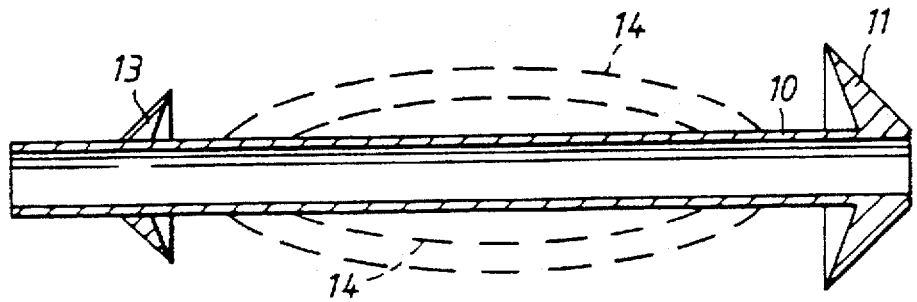

CATHETER COMPRISED OF OR INCLUDING ELECTRICALLY CONDUCTIVE SYNTHETIC MATERIAL

The present application claims the benefit of the priority of earlier filed International Application Number PCT/SE94/00154 which was filed 24 Feb. 1994 (24.02.94), as well as the priority of earlier filed Swedish patent application Number 9300655-9, which was filed 26 Feb. 1993 (26.02.93).

BACKGROUND OF THE INVENTION

The present invention relates to a catheter of the kind defined in the preamble of claim 1 and known from published Swedish specification SE 8902333-7, for instance.

Catheters of this kind are often used particularly as so-called discharge arrest catheters for people suffering from incontinence. Urine incontinence afflicts both men and women, often men and women above the age of forty-five, and it is calculated that at least five-hundred thousand people suffer this loss of evacuative control. In the case of males, urine incontinence can often be caused by an enlarged prostate, although it is normally the annular sphincter in the urethra which become relaxed, therewith leading initially to slight urine incontinence in many cases. The person who suffers from urine incontinence is primarily worried by the thought that any involuntary urine discharge will be smelt by those in his/her vicinity, causing the sufferer to be afraid to venture outdoors and possibly leading to depression. Investigations have shown that practically all people who suffer incontinence are subjected to physical strain. The medical treatments available include prostate surgery, electrical stimulation of the muscles in the urethra, and training of the bladder.

Medical treatment in the form of electrical stimulation of the prostate and/or sphincter in the urethra have been found to have a good effect. The disadvantage with such treatment is that the person suffering incontinence is obliged to seek general care where appropriate means and assistance are provided, although the treatment prescribed will normally take a long time to effect.

The object of the present invention is to provide a urethra insertable catheter with which the urethra muscles which control the discharge of urine are electrically stimulated, and also the prostate of males, wherein the applied voltage is utilized as a muscle stimulant and the heat generated by the electric voltage is used to treat the prostate gland.

The invention takes as its starting point a catheter which comprises an elongated or relatively elongated hollow body which is open at both ends thereof and has a circular cross-sectional shape and which is produced from an appropriate synthetic material, said body presenting along its length at least one annular thickening or swelling which projects radially out from the body and which is intended to lie against the inner walls of the urethra.

SUMMARY OF THE INVENTION

With the intention of solving the aforesaid problem, it is proposed in accordance with the invention that the catheter body and the at least one thickening are both comprised of or include an electrically conductive synthetic material; and in that the end of the catheter body opposite to the catheter insertion end is provided with means for connecting the catheter body to a source of low a.c. voltage.

A source of electric current can be easily connected to a catheter of this construction. This obviates the need for the complicated equipment normally required at present for this purpose. The voltage applied may be a constant or pulsated voltage, as desired. By using a thickening that comprises an electrically non-conductive material and which can be moved axially along the catheter body as described in claim 2, the catheter can be brought to a position in the urethra in which it lies against a relaxed sphincter and therewith stimulate the muscle. According to the invention, the catheter body can also be inserted into the urethra to an extent at which the prostate will be electrically stimulated. It has also been observed medically (inter alia in the journal "Ny Teknik", No. 3, 1993) that certain prostate diseases can be alleviated or cured by subjecting the prostate to heat. It would seem that the inventive catheter is able to provide an effective supportive aid in this latter respect, since the voltage applied can be controlled. The catheter body and its electrically conductive thickening is able to deliver heat to the area concerned, the temperature of which can be controlled and monitored externally.

Other advantages and features of the invention will be apparent from the remaining Claims and also from the following description of an exemplifying embodiment of the invention, which is made with reference to the accompanying drawing, in which

BRIEF DESCRIPTION OF THE DRAWINGS

FIG. 1 is a longitudinal sectional view of a first embodiment of the improved catheter; and FIG. 2 illustrates a second exemplifying embodiment of the inventive catheter.

DESCRIPTION OF THE PREFERRED EMBODIMENT

The inventive catheter includes an elongated or relatively elongated hollow catheter body 10 which is made of an electrically conductive and resilient synthetic material, or from a resilient synthetic material which has been made electrically conductive in manufacture by incorporating electrically conductive material thereinto, such as carbon black, carbon fibres and the like. The catheter body will preferably have a length suitable for use by both men and women.

The illustrated catheter body 10 has an integral thickening 11 at the insertion end of the catheter. The illustrated thickening 11 has a dish-shape and extends circumferentially around said body. The part of the dish-shaped thickening 11 which extends in the axial direction of the catheter body has a length which is greater than the outer diameter of said body. This thickening 11 may be comprised of or include an electrically conductive material. The illustrated exemplifying embodiment of the inventive catheter also includes at least one further, preferably dish-shaped thickening 12 which is spaced axially from the first thickening 11 and is formed integrally with the catheter body 10. This second thickening 12 also has electrically conductive properties preferably of a smaller size than the thickening 11.

According to a preferred embodiment, the catheter also includes a third, annular thickening 13, as illustrated. This third thickening can be displaced axially along the catheter body 10. In this case, the thickening 13 is preferably capable of being press-fitted onto the catheter body 10, so as to enable said thickening to be held in selected positions along said body. It will be understood that the thickening which is intended for displacement along the catheter body will not be electrically conductive and is intended to provide means for limiting the extent to which the catheter body can be inserted.

In the illustrated embodiments, the respective forwardly located thickenings include "wings" which are angled rearwardly with regard to the insertion direction, while the rearward thickening is provided with "wings" which are angled in the opposite direction.

As before mentioned, a catheter of the aforedescribed kind can be easily connected to a low a.c. voltage source (not shown), and the applied voltage may be pulsating or constant, or even of the microwave kind. The current source can be connected to one end of the catheter with the aid of conventional battery terminal clamps.

The aforedescribed thickenings 11, 12 on the catheter body 10 may also be combined with or optionally replaced by a known inflatable bladder, as indicated in broken lines in FIG. 2 and referenced 14. Such a bladder 14 may have a varying axial extension.

I claim:

1. A catheter for insertion into a patient's urethra, which comprises an elongated open-ended hollow body of circular cross-section having proximal and distal ends, wherein the catheter body has provided along its length one or more resilient annular projections which project radially outwards and are intended to contact the inner walls of the urethra, the catheter body and each projection are electrically conductive, and the proximal end of the catheter is capable of being connected to a low voltage source; and wherein at least one of the projections comprises a plate-like bulge (11) permanently fixed to the proximal end of the catheter, characterized by a further, annular bulge (13) fitted to the catheter body (10) and which is movable along the length of the catheter body and is made of an electrically nonconductive material.

2. The catheter according to claim 1, characterized in that at least one of the projections comprises an elongated resilient bulge (14) which encircles the catheter body.

3. The catheter according to claim 2, characterized in that the elongated bulge (14) has a length which is equal to or longer than the length of half the catheter body (10).

4. The catheter according to claim 3, characterized in that the elongated bulge (14) extends between two adjacent, dish-shaped projections (12, 13), of which one may be movable axially on the catheter body.

5. The catheter according to claim 1, characterized in that the catheter body (10) is provided on selected areas thereof with a substance which will protect the mucous membrane with which the catheter comes in contact.

6. The catheter according to claim 1, wherein the electrical conductive material is selected from the group consisting of carbon black and carbon fiber.

* * * * *